United States Patent [19]
Comparetto

[11] 4,320,752
[45] Mar. 23, 1982

[54] MULTI-BAND OR NETWORK MALE CONTRACEPTIVE

[76] Inventor: John E. Comparetto, 108 Cropper St., Chincoteaque, Va. 23336

[21] Appl. No.: 62,073

[22] Filed: Jul. 30, 1979

[51] Int. Cl.³ .............................................. A61F 5/42
[52] U.S. Cl. .................................. 128/132 R; 128/294
[58] Field of Search .................. 128/294, 132 R, 260, 128/138 R, 79

[56] References Cited
U.S. PATENT DOCUMENTS 3,648,700  3/1972  Warner ................................. 128/294
3,677,225  7/1972  Czirely ............................ 128/132 R
3,951,141  4/1976  Kopelowicz ........................ 128/294
4,074,712  2/1978  Wright ................................. 128/79

FOREIGN PATENT DOCUMENTS 110234  7/1899  Fed. Rep. of Germany ...... 128/294

Primary Examiner—John D. Yasko
Attorney, Agent, or Firm—James C. Wray

[57] ABSTRACT

A network of adhesive bands seals a semen receptacle to prevent sperm from escaping from this receptacle. The receptacle and adhesive network covers the penile orifice. The receptacle also has one-way valve systems.

14 Claims, 15 Drawing Figures

FIG. 1
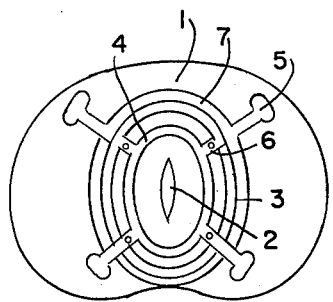
FIG. 2
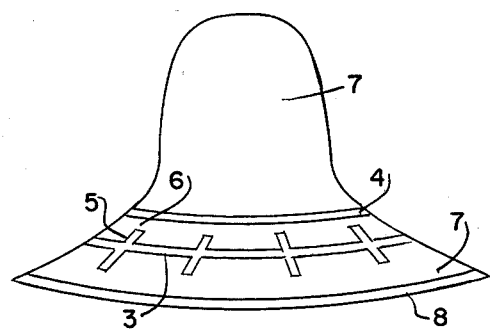
FIG. 3
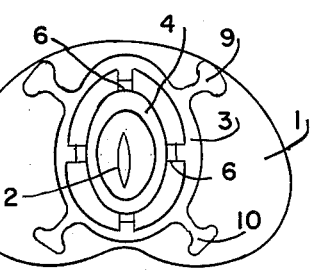
FIG. 4
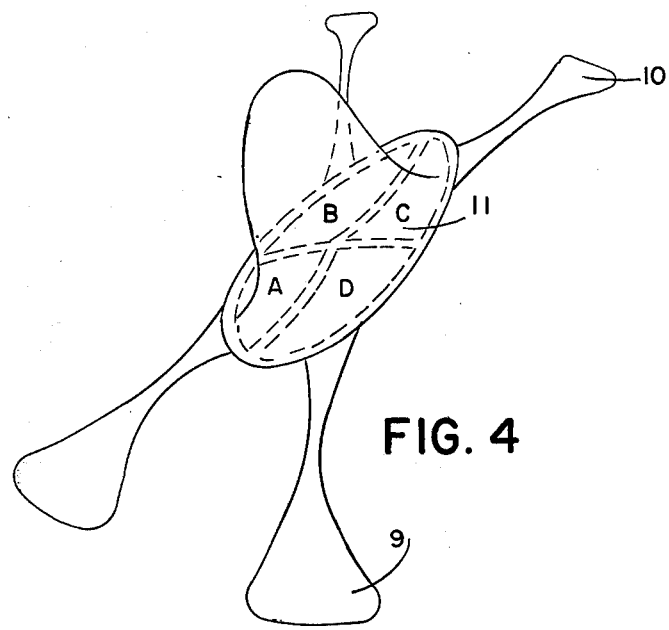
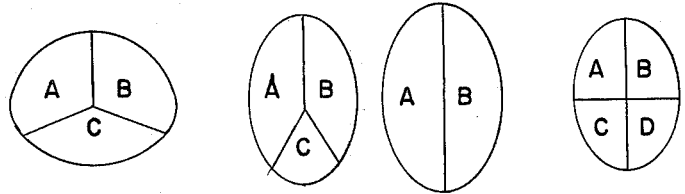
FIG. 5

FIG. 10
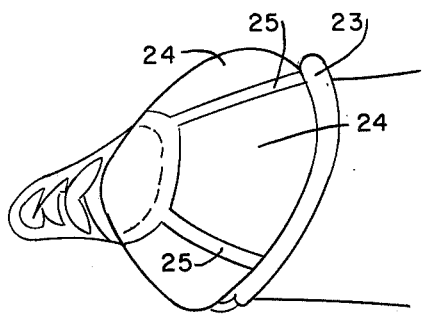
FIG. 11
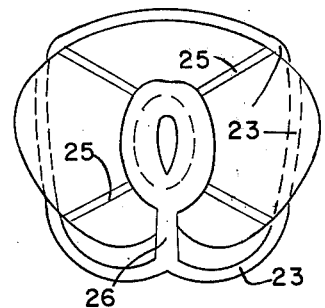
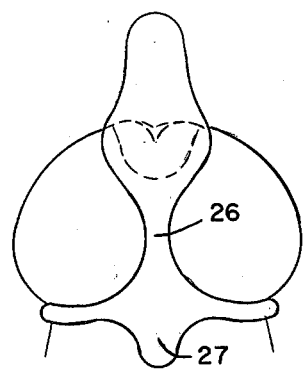
FIG. 12
FIG. 13
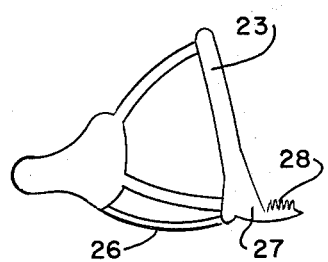

MULTI-BAND OR NETWORK MALE CONTRACEPTIVE

BACKGROUND OF THE INVENTION

Modern day male contraceptives are uncomfortable and mechanically reduce the pleasure for both parties in sexual intercourse. The alternative to male contraceptives are the female contraceptives such as the diaphram, that are tedious to place and sometimes uncomfortable for both parties. The contraceptive pill for the female has many untoward effects that have been made apparent through research and study. This has stimulated the pharmaceutical interests to find a pill that would be suitable for the male. The safety of such an oral or injectable contraceptive for the male has not been proven safe and if we are to learn a lesson from the side effects of the female hormonal contraceptive that have become apparent after long-term use, this new hormonal approach for the male may prove to be equally dangerous. This invention offers an alternative for all the above.

BRIEF DESCRIPTION OF THE DRAWINGS

FIG. 1 is a frontal view of the device on the penis.
FIG. 2 is a side view of the device.
FIG. 3 is another frontal view of the device with anchoring tabs.
FIG. 4 is a perspective view of the device with anchoring tabs and one-way valve system.
FIG. 5 depicts alternate one-way valve systems.
FIG. 10 depicts a side view of anchor ring and harness straps.
FIG. 11 shows a frontal perspective view of ring and strap embodiment of the invention.
FIG. 12 shows a ventral view of the device of FIGS. 10 and 11 with ventral extension.
FIG. 13 shows a side view of FIG. 12 with setae.

OBJECTS OF THE INVENTION

Figure 6:
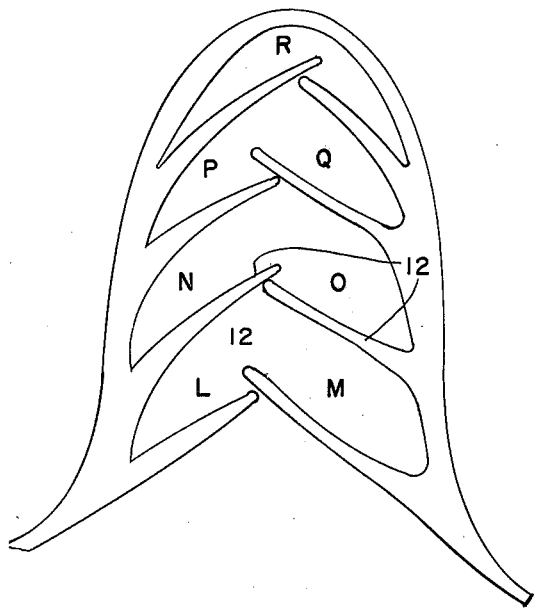
FIG. 6 is a cross-sectional view of an overlapping one-way valve system.

An object of the invention is to provide a safe form of contraception while allowing for a maximum of sensation.

Another object of the invention is to mechanically trap semen using adhesive seals.

A further object of the invention is to trap the semen within one-way valve systems.

An additional object of the invention is to afford adhesive means to hold reusable receptacle means.

DETAILED DESCRIPTION OF THE INVENTION

Upon the glans of the penis 1, receptacle 7 is placed covering the penile orifice 2 as seen in FIG. 1. Concentric rings 3, 4, and 8, as well as tabs 5 of FIGS. 1 and 2 are attached by incorporation into the latex or rubber receptacle or by an adhesive method to the inside of this receptacle. These concentric rings and tabs have an adhesive side that faces the penis and in the aforementioned variation of the invention, an additional adhesive side to attach to the receptacle. In packaging, the penis side adhesive will be protected by a peel-off type of paper. Sections 6 of FIGS. 1, 2, and 3 show areas where there is no adhesive coating. These areas serve to separate the concentric adhesive rings and tabs to allow for a lack of continuity that affords a failsafe mechanism in case the inner ring leaks. With the skin adherents that we have today, this inner concentric ring would probably not leak. In the event that it did, there must be a break of adhesive continuity otherwise the leakage might grow to the outer rings with greater facility.

In FIG. 3, adhesive ventral tabs 10 and dorsal tabs 9 serve to anchor the apparatus to the glans of the penis. FIG. 4 shows a perspective view of the receptacle with dorsal and ventral tabs as well as a one-way valve system at the base of the conical portion of the receptacle.

FIG. 5 shows a series of different one-way valve configurations.

FIG. 6 is a cross-sectional view of an overlapping system of valves. Each valvular flap 12 overlaps the other in a one-way system trapping semen in receptacle spaces L, M, N, O, P, Q, R. These valve leafs start from the base of the receptacle and are contiguous with the receptacle and move apically overlapping one another. The compartments formed by these flaps can be partially filled with a spermatocide.

Figure 7A:
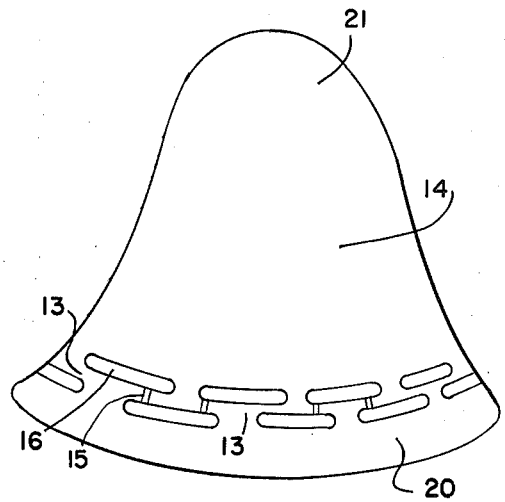
FIG. 7A shows another embodiment of the invention.

FIG. 7A shows another embodiment of the invention having a reusable receptacle 14 having overlapping cut-out sections 16 with interconnecting open sections 15. It also has non-interconnecting segments 13. Segments 13 being confluent with periphery 20 as well as conical section 21 of the receptacle.

Figure 7B:
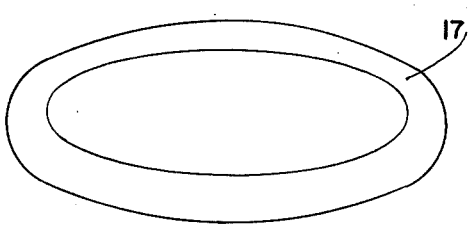
FIG. 7B shows the adhesive portion of 7A.

FIG. 7B shows adhesive ring which fits over the top of the reusable receptacle 14 and adheres, through the opening spaces 16 and 15, to the penis. After intercourse, the adhesive is thrown away and the receptacle is washed and ready for use.

Figure 8:
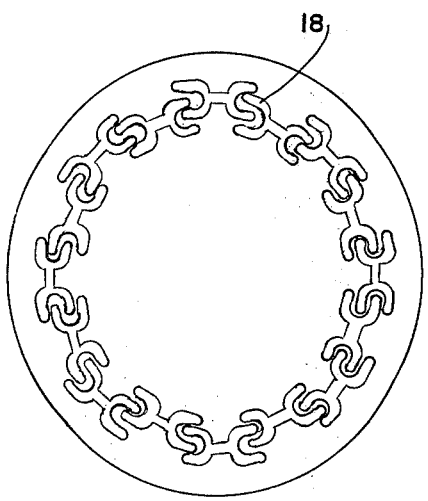
FIG. 8 shows yet another embodiment of the invention.

FIG. 8 is another embodiment of the invention showing overlapping segments 18. The overlapped segments 18 of FIG. 8 are open areas through which the ring 17 of FIG. 7B adheres to the penis keeping the receptacle in place.

Figure 9A:
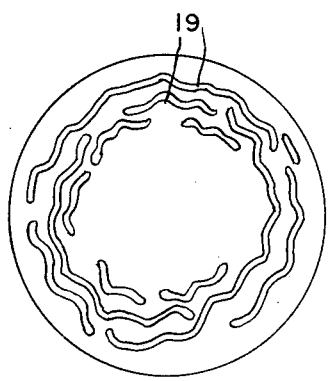
FIG. 9A and B illustrates additional seal configurations.
Figure 9B:
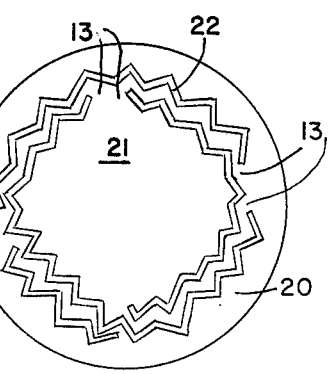

FIGS. 9A and B show additional configurations of rubber cut-outs 19 and 22 with areas of receptacle 21 having continuity at areas 13 with periphery 20. The areas of adhesive would be of necessity, thin areas so as to keep the amount of the adherence to the penile skin at a minimum. The adhesive contraceptive will come off readily as the erection diminishes. With the use of adhesives of great elasticity, the contraceptive can be placed on the penis prior to obtaining an erection. In this case, the contraceptive would need to be peeled off. Peeling off the adhesive seal would be expedient but possibly too painful for men with a low pain threshold. For these individuals soaking in a bath will facilitate removal.

FIGS. 10 and 11 show yet another embodiment of the invention having an elastic harness ring 23 with open areas 24 for exposing penile skin. This variation of the invention would be made with no adhesive rings or as little as one.

The device can be made to fit on the flaccid penis or on the erect penis by anchoring with elastic ring 23, FIGS. 10 and 11. The ring 23 fits behind the penile cap, the corona glandis, around the neck of the penis. The receptacle may have only one adhesive band or none. The receptacle is attached to ring 23 by straps 25 and ventral strap 26 (FIG. 11). The ventral strap 26 helps to align the receptacle over the orifice. Strap 26 fits between the anatomical surface division of the glans penis just distal to the ventral sensitive area of the glans called the frenulum. Strap 26 unites with ring 23 at this distal point. In individuals who experience early climax, a proximal extention 27 (FIG. 12) of strap 26 and ring 23 could be made to cover this area with non-sensitive material, for example, thick layer rubber. For normal maximum sensation, this area will remain bare. The converse situation to the early climax individual would be those who require extra stimulation. The extention 27 will then be fitted with small setae projections 28 of FIG. 13 that would mechanically stimulate the sensitive frenular area during intercourse.

What is claimed is:

1. A receptacle apparatus of impervious to semen material with overlapping leaves forming valves and; adhesive peripheral areas for adherence to the glans penis while covering the penile orifice, where said peripheral areas have concentric adhesive rings with breaks in adhesive continuity.

2. The apparatus of claim 1 wherein the concentric peripheral rings of adhesive are attached by incorporation or by adhesive to the inner peripheral areas of the receptacle, but also by having adhesive on the opposite side of these rings to attach to penile skin.

3. The apparatus of claim 1 having a continuous band of adhesive as described in claim 2, but being of irregular or non-circular shape.

4. The apparatus of claim 1 having adhesive tabs helping to anchor one or more of the contiguous rings.

5. The apparatus of claim 1 having overlapping leaves forming one-way valve flaps at its base.

6. The apparatus of claim 1 having a multiple of one-way valve flaps forming overlapping leaves from its base to apex.

7. The apparatus of claim 1 having compartments formed by the valve flaps of claim 7 containing a spermatocide.

8. The apparatus of claim 1 having leaves forming valves and having overlapping cut-away segments that allows for the placement of an adhesive band to cover these cut-out segments.

9. The cut-out segments of claim 8 overlap and connect excluding areas of material impervious to semen confluent from periphery to apex.

10. The adhesive band of claim 8 contacts the penile tissues through said cut-outs segments.

11. The cut-outs segments of claims 8 comprise any shaped configuration having a lack of continuity of each overlapped area assuring continuity of the periphery to the apex.

12. The apparati of claims 5, 6, and 7 having overlapping leaves forming valves and an elastic anchoring ring and holding straps.

13. The apparatus of claim 12 having a ventral extention of insensitive material to cover highly sensitive ventral skin.

14. The apparatus of claim 12 having stimulating setae to mechanically stimulate the sensitive ventral areas.

* * * * *